(12) United States Patent
Haibara et al.

(10) Patent No.: US 8,778,085 B2
(45) Date of Patent: Jul. 15, 2014

(54) DISSOLVED NITROGEN CONCENTRATION MONITORING METHOD, SUBSTRATE CLEANING METHOD, AND SUBSTRATE CLEANING APPARATUS

(75) Inventors: Teruo Haibara, Hikari (JP); Etsuko Kubo, Yokkaichi (JP); Yoshihiro Mori, Nakagyo-ku (JP); Masashi Uchibe, Izumo (JP)

(73) Assignee: Siltronic AG, Munich (DE)

( * ) Notice: Subject to any disclaimer, the term of this patent is extended or adjusted under 35 U.S.C. 154(b) by 0 days.

(21) Appl. No.: 13/995,568

(22) PCT Filed: Dec. 13, 2011

(86) PCT No.: PCT/EP2011/072639
§ 371 (c)(1),
(2), (4) Date: Jun. 19, 2013

(87) PCT Pub. No.: WO2012/084610
PCT Pub. Date: Jun. 28, 2012

(65) Prior Publication Data
US 2013/0263887 A1    Oct. 10, 2013

(30) Foreign Application Priority Data

Dec. 20, 2010 (JP) ................................ 2010-283078

(51) Int. Cl.
*B08B 3/12* (2006.01)
(52) U.S. Cl.
USPC ............... 134/1; 134/184; 73/19.01; 73/19.1; 73/19.03; 73/61.41; 73/61.79; 73/64.53; 436/106; 436/114; 436/127; 436/136; 436/138
(58) Field of Classification Search
CPC ... G01N 29/02; G01N 29/024; G01N 29/028; G01N 29/032; G01N 29/036; G01N 2291/02433; B08B 3/04; B08B 3/12; B08B 3/10

USPC ............. 73/19.01, 19.1, 19.03, 61.41, 61.79, 73/64.53; 436/106, 114, 127, 136, 138; 134/1, 184
See application file for complete search history.

(56) References Cited

U.S. PATENT DOCUMENTS

| 5,144,831 A | 9/1992 | Hale et al. |
| 6,058,945 A * | 5/2000 | Fujiyama et al. ............... 134/1.3 |
| 2003/0150477 A1 | 8/2003 | Suzuki |

FOREIGN PATENT DOCUMENTS

| JP | H03 176640 A | 7/1991 |
| JP | H10 335294 A | 12/1998 |
| JP | 2000 131 308 A | 5/2000 |
| JP | 2003 234320 A | 8/2003 |
| JP | 2006 310456 A | 11/2006 |
| JP | 2009054919 A | 3/2009 |

* cited by examiner

*Primary Examiner* — Bibi Carrillo
(74) *Attorney, Agent, or Firm* — Leydig, Voit & Mayer, Ltd.

(57) ABSTRACT

A dissolved nitrogen concentration monitoring method is used for monitoring a dissolved nitrogen concentration of a cleaning liquid when an ultrasonic wave is irradiated onto the cleaning liquid in which a substrate is dipped. The method includes measuring an amount of increase of a dissolved oxygen concentration of the cleaning liquid resulting from an oxygen molecule generated from a water molecule as a result of a radical reaction caused by ultrasonic wave irradiation. A dissolved nitrogen concentration of the cleaning liquid is calculated from the measured amount of increase of dissolved oxygen concentration based on a predetermined relationship between a dissolved nitrogen concentration and an amount of increase of dissolved oxygen concentration.

9 Claims, 7 Drawing Sheets

DISSOLVED NITROGEN CONCENTRATION MONITORING METHOD, SUBSTRATE CLEANING METHOD, AND SUBSTRATE CLEANING APPARATUS

CROSS REFERENCE TO RELATED APPLICATIONS

This application is a U.S. National Phase application under 35 U.S.C. §371 of International Application No. PCT/EP2011/072639, filed on Dec. 13, 2011, and claims benefit to Japanese Patent Application No. JP 2010-283078, filed on Dec. 20, 2010. The International Application was published in English on Jun. 28, 2012, as WO 2012/084610 A1 under PCT Article 21 (2).

FIELD

The present invention relates to a dissolved nitrogen concentration monitoring method, substrate cleaning method, and substrate cleaning apparatus for a wafer cleaning process.

More specifically, the present invention relates to a dissolved nitrogen concentration monitoring method, substrate cleaning method, and substrate cleaning apparatus for monitoring the dissolved nitrogen concentration of a cleaning liquid into which a substrate, such as a wafer, is dipped.

BACKGROUND

In general, in a production process of a substrate, such as a wafer, a substrate cleaning process using dipping, single-wafer, or like method is performed to remove factors responsible for defect of semiconductor devices. Such factors include organic substances, metal impurities, particles (fine particles), and chemical oxide films.

A substrate cleaning process employs various types of cleaning methods depending on the purpose. In particular, when the dipping method is employed to remove particles, a substrate is dipped into a cleaning liquid contained in a cleaning bath, and ultrasonic waves are irradiated onto the cleaning liquid where the substrate is dipped. Such ultrasonic waves are called megasonic waves, whose frequency range is around 1 MHz. It is generally recognized that use of ultrasonic waves in a frequency range of around 1 MHz reduces damage to the substrate and increases the effectiveness of cleaning micro particles of submicron sizes on the substrate.

When megasonic waves are irradiated onto ultrapure water to remove particles from the substrate, the particle removal efficiency is known to be affected by the dissolved nitrogen concentration of a cleaning liquid. Specifically, in a specific range of the dissolved nitrogen concentration of a cleaning liquid, the particle removal efficiency for substrate increases. If the dissolved nitrogen concentration of a cleaning liquid is monitored and controlled to be in a certain range during the cleaning process, effective removal of particles is theoretically possible.

In a hitherto known method, gas components contained in a fluid medium are introduced into a container through a polymer membrane, and the concentration of the gas components are calculated based on changes in the thermal conductivity in the container (Japanese Laid-open Patent Publication (Kokai) No. H03-176640). This method has been employed to monitor the dissolved nitrogen concentration of a cleaning liquid.

Alternatively, Irradiation of ultrasonic waves onto sample water containing nitrogen gas generates hydrogen radicals derived from water molecules. The hydrogen radicals react with the nitrogen gas, and nitrogen compounds ($NO_x$—, $NH_4^+$) are produced. A method based on this mechanism has been proposed for calculating the dissolved nitrogen concentration of a sample (Japanese Laid-open Patent Publication (Kokai) No. 2003-131308). In this method, after radical treatment is performed for sample water by means of ultrasonic wave irradiation, the ion amount derived from nitrogen atoms is measured by a resistivity meter, and the dissolved nitrogen concentration of the sample is calculated based on the ion amount.

SUMMARY OF THE INVENTION

In an embodiment, the present invention provides a dissolved nitrogen concentration monitoring method for monitoring a dissolved nitrogen concentration of a cleaning liquid when an ultrasonic wave is irradiated onto the cleaning liquid in which a substrate is dipped. The method includes measuring an amount of increase of a dissolved oxygen concentration of the cleaning liquid resulting from an oxygen molecule generated from a water molecule as a result of a radical reaction caused by ultrasonic wave irradiation. A dissolved nitrogen concentration of the cleaning liquid is calculated from the measured amount of increase of dissolved oxygen concentration based on a predetermined relationship between a dissolved nitrogen concentration and an amount of increase of dissolved oxygen concentration.

BRIEF DESCRIPTION OF THE DRAWINGS

The present invention will be described in even greater detail below based on the exemplary figures. The features and advantages of various embodiments of the present invention will become apparent by reading the following detailed description with reference to the attached drawings which illustrate the following:

FIG. 5(a) is a diagram plotting each of the ultrasonic output power levels.

FIG. 6(a) is a diagram plotting each of the overflow rates.

DETAILED DESCRIPTION

Figure 1:
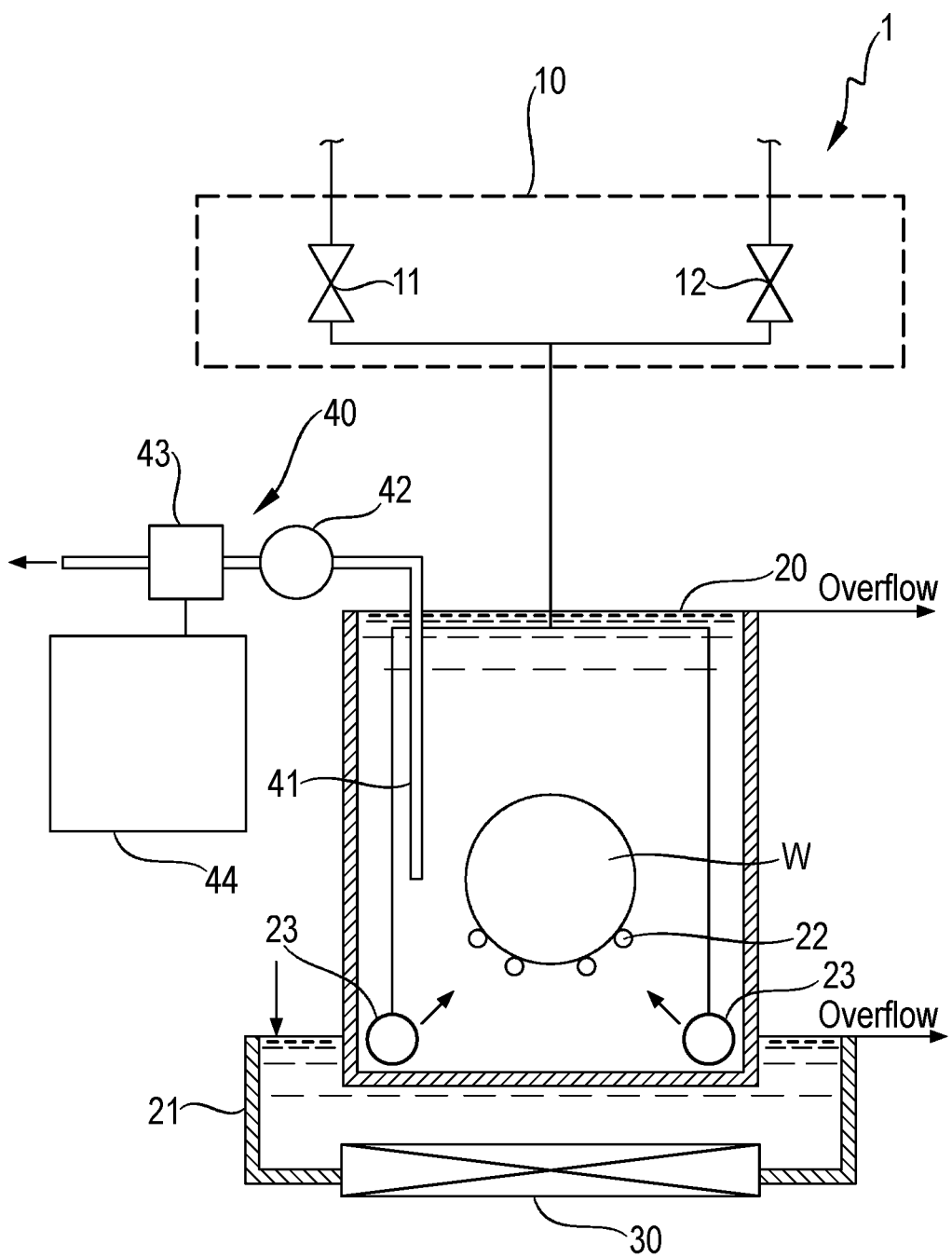
FIG. 1 is a diagram schematically showing a configuration of an ultrasonic cleaning apparatus to which a monitoring method according to an embodiment of the present invention is applied.

In the method according to Japanese Laid-open Patent Publication (Kokai) No. H03-176640, when a gas whose thermal conductivity is close to that of nitrogen, e.g., oxygen, is contained in gas components, the thermal conductivity of nitrogen cannot be accurately measured due to effects of the thermal conductivity of oxygen. This raises the problem that the dissolved nitrogen concentration of a cleaning liquid cannot be accurately measured.

To address this problem, a different method for calculating the dissolved nitrogen concentration has been proposed. In this method, the dissolved oxygen concentration of gas components are measured using the polarography method or the like, and measurements of the dissolved oxygen concentration are used to correct the value of the dissolved nitrogen concentration for calculation thereof. However, in this method, measurement of the dissolved oxygen concentration needs to be performed in addition to measurement of the dissolved nitrogen concentration, which requires complicated operations. There is also a cost problem arising from very expensive dissolved nitrogen concentration meters that have been conventionally used. In addition, this method requires more than 10 seconds for each measurement of the thermal conductivity of gas components. As the dissolved nitrogen concentration cannot be monitored real-time, the monitoring is not accurate.

Also, in the method according to Japanese Laid-open Patent Publication (Kokai) No. 2003-131308, the ion amount derived from nitrogen atoms cannot be accurately measured with presence of another component ionized in sample water, and the dissolved nitrogen concentration of the sample water cannot be accurately calculated. As this method is focused only on changes in the amount of nitrogen compounds due to ultrasonic wave irradiation, but not on changes in the dissolved oxygen concentration.

An aspect f the present invention is to provide a dissolved nitrogen concentration monitoring method, substrate cleaning method, and substrate cleaning apparatus which make it possible to accurately monitor the dissolved nitrogen concentration of a cleaning liquid in real-time without complicated operations and reduce the cost.

To solve the above problems, according to the present invention, there is provided a dissolved nitrogen concentration monitoring method directed to monitoring a dissolved nitrogen concentration of a cleaning liquid when an ultrasonic wave is irradiated onto the cleaning liquid in which a substrate is dipped. The dissolved nitrogen concentration monitoring method is characterized by comprising the steps of: measuring an increase amount of dissolved oxygen concentration of the cleaning liquid, which is due to an oxygen molecule generated from a water molecule as a result of a radical reaction caused by ultrasonic wave irradiation; and calculating a dissolved nitrogen concentration of the cleaning liquid from the measured increase amount of dissolved oxygen concentration based on a predetermined relationship between a dissolved nitrogen concentration and an increase amount of dissolved oxygen concentration.

Also, the dissolved nitrogen concentration of the cleaning liquid is calculated from an increase amount of dissolved oxygen concentration measured by a dissolved oxygen concentration meter based on dissolved gas information indicating a relationship between the dissolved nitrogen concentration of the cleaning liquid and the increase amount of dissolved oxygen concentration thereof.

In addition, the dissolved gas information is compiled in advance for each of cleaning conditions of the substrate.

Furthermore, the cleaning conditions of the substrate include an ultrasonic output power level.

The dissolved gas information indicates that as the ultrasonic output power level increases, the increase amount of dissolved oxygen concentration corresponding to a specific dissolved nitrogen concentration increases.

As well, the cleaning conditions of the substrate include an overflow rate of a cleaning liquid.

The dissolved gas information indicates that as the overflow rate decreases, a rate of change in the increase amount of dissolved oxygen concentration increases with respect to the dissolved nitrogen concentration.

Moreover, it is preferable that the cleaning liquid is water.

The substrate cleaning method of the present invention is a method for cleaning a substrate by irradiating an ultrasonic wave onto a cleaning liquid into which the substrate is dipped. In this method, the increase amount of the dissolved oxygen concentration in the cleaning liquid, which is due to an oxygen molecule generated from a water molecule as a result of a radical reaction caused by ultrasonic wave irradiation, is measured. In turn, the mixture ratio of a cleaning liquid with dissolved nitrogen gas, which is to be introduced into a cleaning bath, is adjusted so that the increase amount of the dissolved oxygen concentration is in a specific range where the cleaning performance is high.

The substrate cleaning apparatus of the present invention is an apparatus for cleaning a substrate by irradiating an ultrasonic wave to a cleaning liquid into which the substrate is dipped. This apparatus measures the increase amount of the dissolved oxygen concentration in the cleaning liquid, which is due to an oxygen molecule generated from a water molecule as a result of a radical reaction caused by ultrasonic wave irradiation. In turn, this apparatus adjusts the mixture ratio of a cleaning liquid with dissolved nitrogen gas, which is to be introduced into a cleaning bath, so that the increase amount of the dissolved oxygen concentration is in a specific range where the cleaning performance is high.

According to the present invention, an increase amount of dissolved oxygen concentration, which is due to oxygen molecules generated from water molecules as a result of a radical reaction caused by ultrasonic wave irradiation, is measured. Then the dissolved nitrogen concentration of a cleaning liquid is calculated from the measured increase amount of dissolved oxygen concentration based on a predetermined relationship between the dissolved nitrogen concentration and the increase amount of dissolved oxygen concentration. As the dissolved nitrogen concentration can be calculated by measuring the dissolved oxygen concentration of a cleaning liquid, no complicated operation is required. Since the relationship between the dissolved nitrogen concentration and the increase amount of dissolved oxygen concentration is predetermined, the dissolved nitrogen concentration can be accurately calculated using this relationship. Cost reduction is also possible as use of expensive dissolved nitrogen concentration meters is not necessary, and real-time measurement is possible since the dissolved oxygen concentration can be measured using a dissolved oxygen concentration meter of the polarography type or the like. In addition to cost reduction, real-time accurate monitoring of the dissolved nitrogen concentration of a cleaning liquid can be made without complicated operations.

The relationship between the dissolved nitrogen concentration of a cleaning liquid and the increase amount of dissolved oxygen concentration thereof is indicated by dissolved gas information. Based on this information, the dissolved nitrogen concentration of the cleaning liquid is calculated from the increase amount of dissolved oxygen concentration measured by a dissolved oxygen concentration meter. As an inexpensive dissolved oxygen concentration meter can be used for measurement of the dissolved nitrogen concentration, further cost reduction is possible.

Since the dissolved gas information is produced in advance for each of substrate cleaning conditions, even when a cleaning condition is changed, the dissolved nitrogen concentration of a cleaning liquid can be accurately calculated.

The aforementioned substrate cleaning conditions include the ultrasonic output power level. Even when the output power level of ultrasonic waves irradiated onto a cleaning liquid is changed, the dissolved nitrogen concentration can be accurately calculated based on the dissolved gas information that corresponds to the changed output power level.

The aforementioned dissolved gas information indicates that as the ultrasonic output power level increases, the increase amount of dissolved oxygen concentration corresponding to a specific dissolved nitrogen concentration increases. By increasing the ultrasonic output power level, the calculatable value of the dissolved nitrogen concentration increases, and the accuracy of measurement thereof increases.

Also, the aforementioned substrate cleaning conditions include the overflow rate of a cleaning liquid. Even when the overflow rate of a cleaning liquid is changed, the dissolved nitrogen concentration can be accurately calculated based on the dissolved gas information that corresponds to the changed overflow rate.

The aforementioned dissolved gas information indicates that as the overflow rate decreases, the rate of change in the increase amount of dissolved oxygen concentration increases with respect to the dissolved nitrogen concentration. By decreasing the overflow rate, the dissolved nitrogen concentration can be accurately calculated.

According to the present invention, the mixture ratio of a cleaning liquid with dissolved nitrogen gas, which is to be introduced into a cleaning bath, is adjusted so that the increase amount of the dissolved oxygen concentration is in a specific range where the cleaning performance is high. Substrate cleaning with a high particle removal efficiency can be achieved without using a dissolved nitrogen concentration meter.

The present invention will now be described in detail below with reference to the drawings showing preferred embodiments thereof.

Figure 2:
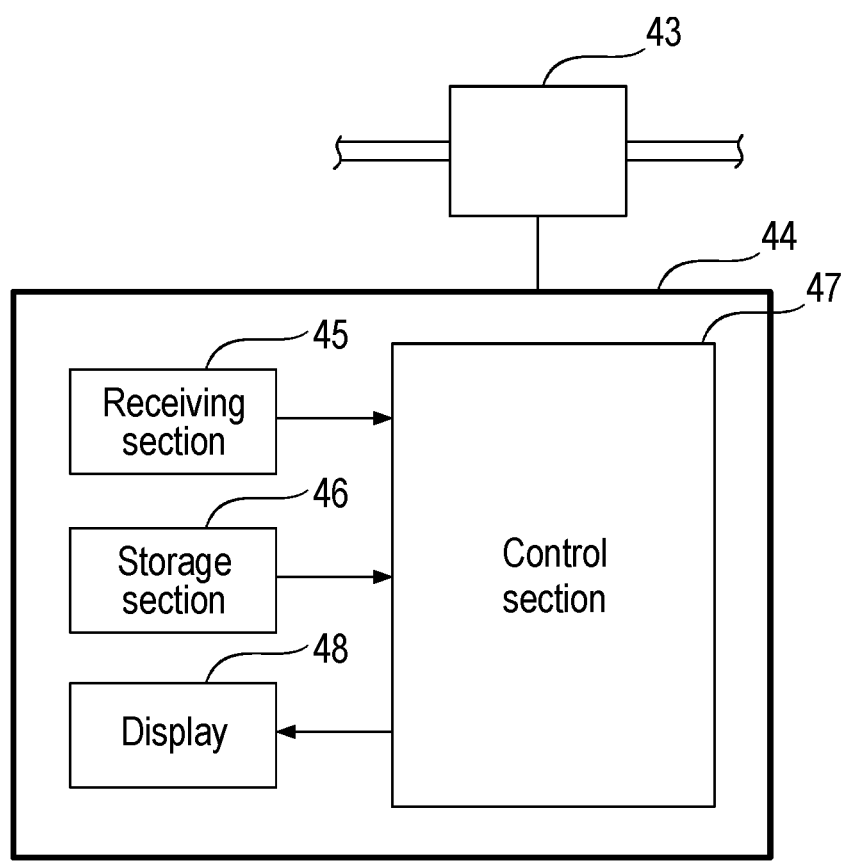
FIG. 2 is a block diagram showing a configuration of a monitoring unit that performs a monitoring method according a present embodiment.

FIG. 1 is a diagram schematically showing a configuration of an ultrasonic cleaning apparatus to which a monitoring method according to an embodiment of the present invention is applied. FIG. 2 is a block diagram showing a configuration of a monitoring unit that performs the monitoring method according the present embodiment.

As shown in FIG. 1, an ultrasonic cleaning apparatus 1 is comprised of a supply unit 10, a coupling bath 21, an irradiation unit 30, and a monitoring unit 40. The supply unit 10 supplies a cleaning liquid, such as ultrapure water, to a cleaning bath 20. The coupling bath 21 houses the cleaning bath 20. The irradiation unit 30 is disposed at the bottom of the coupling bath 21 and irradiates ultrasonic waves onto inside the cleaning bath 20. The monitoring unit 40 monitors the dissolved nitrogen concentration of the cleaning liquid supplied to inside the cleaning bath 20.

The supply unit 10 has a first supply valve 11 that supplies ultrapure water with dissolved nitrogen gas to a below-described mixed bath and a second supply valve 12 that supplies degassed ultrapure water to the below-described mixed bath. The ultrapure water with dissolved nitrogen gas and the degassed ultrapure water are mixed at a location downstream from the first supply valve 11 and the second supply valve 12.

The mixed pure water is supplied to a liquid introduction pipe, which will be described below, via a pipe installed inside the cleaning bath 20. By adjusting the amount of the valve opening of the first supply valve 11 and the second supply valve 12, the dissolved nitrogen concentration of the ultrapure water to be supplied to inside the cleaning bath 20 and the flow rate of the supplied water are controlled.

The cleaning bath 20 has a wafer holder 22 that holds inside a wafer W, e.g., a semiconductor wafer, and stores the mixed ultrapure water while the wafer holder 22 is holding a substrate W. The substrate W is thereby dipped into the mixed cleaning liquid in the cleaning bath 20. Liquid introduction pipes 23 are arranged at a lower portion of the cleaning bath 20, so that the liquid introduction pipes 23 supply the mixed ultrapure water to the cleaning bath at a predetermined overflow rate. The coupling bath 21 is connected with a supply line (not shown) other than the supply unit 10 and is supplied with water at a predetermined overflow rate.

By oscillating ultrasonic waves at frequencies of 20 kHz to 2 MHz and at watt densities of 0.05 to 7.0 W/cm2, the irradiation unit 30 irradiates the ultrasonic waves onto the mixed ultrapure water in the cleaning bath 20 via the water stored in the coupling bath 21. The wafer W dipped in the mixed ultrapure water is thereby cleaned. It is preferable to use ultrasonic waves whose frequency ranges from 400 kHz to 1 MHz.

The monitoring unit 40 includes a sampling pipe 41, a pump 42, a dissolved oxygen concentration meter 43, and a determination unit 44. The sampling pipe 41 extracts the mixed ultrapure water in a predetermined amount. The pump 42 is connected to the sampling pipe 41 and supplies a predetermined amount of mixed ultrapure water to a below-described dissolved oxygen concentration meter. The dissolved oxygen concentration meter 43, which is connected to the pump 42 at a location downstream thereof, measures the dissolved oxygen concentration of the mixed ultrapure water and sends electric signals corresponding to the measured dissolved oxygen concentration to the below-described determination unit. The determination unit 44 determines the dissolved nitrogen concentration in the cleaning bath 20 based on the electric signals sent from the dissolved oxygen concentration meter 43. The dissolved oxygen concentration meter 43 is, for example, a dissolved oxygen concentration meter using the polarography method. In the polarography method, two types of metals are dipped in an electrolyte solution, and a certain voltage is applied between the two metals to cause an oxidation reduction reaction. Then the current proportional to the dissolved oxygen concentration of the electrolyte solution is measured.

As shown in FIG. 2, the determination unit 44 has a receiving section 45, a storage section 46, a control section 47, and a display 48. The receiving section 45 receives electric signals from the dissolved oxygen concentration meter 43. The storage section 46 stores dissolved gas information, which indicates a predetermined relationship between the dissolved nitrogen concentration and the increase amount of dissolved oxygen concentration. The control section 47 calculates the increase amount of dissolved oxygen concentration based on the electric signals received from the receiving section 45 when ultrasonic waves are irradiated. Also, the control section 47 calculates the dissolved nitrogen concentration of a cleaning liquid from the increase amount of dissolved oxygen concentration measured by a dissolved oxygen concentration meter based on the dissolved gas information, which indicates the relationship between the dissolved nitrogen concentration of the cleaning liquid and the increase amount of dissolved oxygen concentration thereof. The display 48 displays the dissolved nitrogen concentration calculated by the control section 47.

Figure 7:
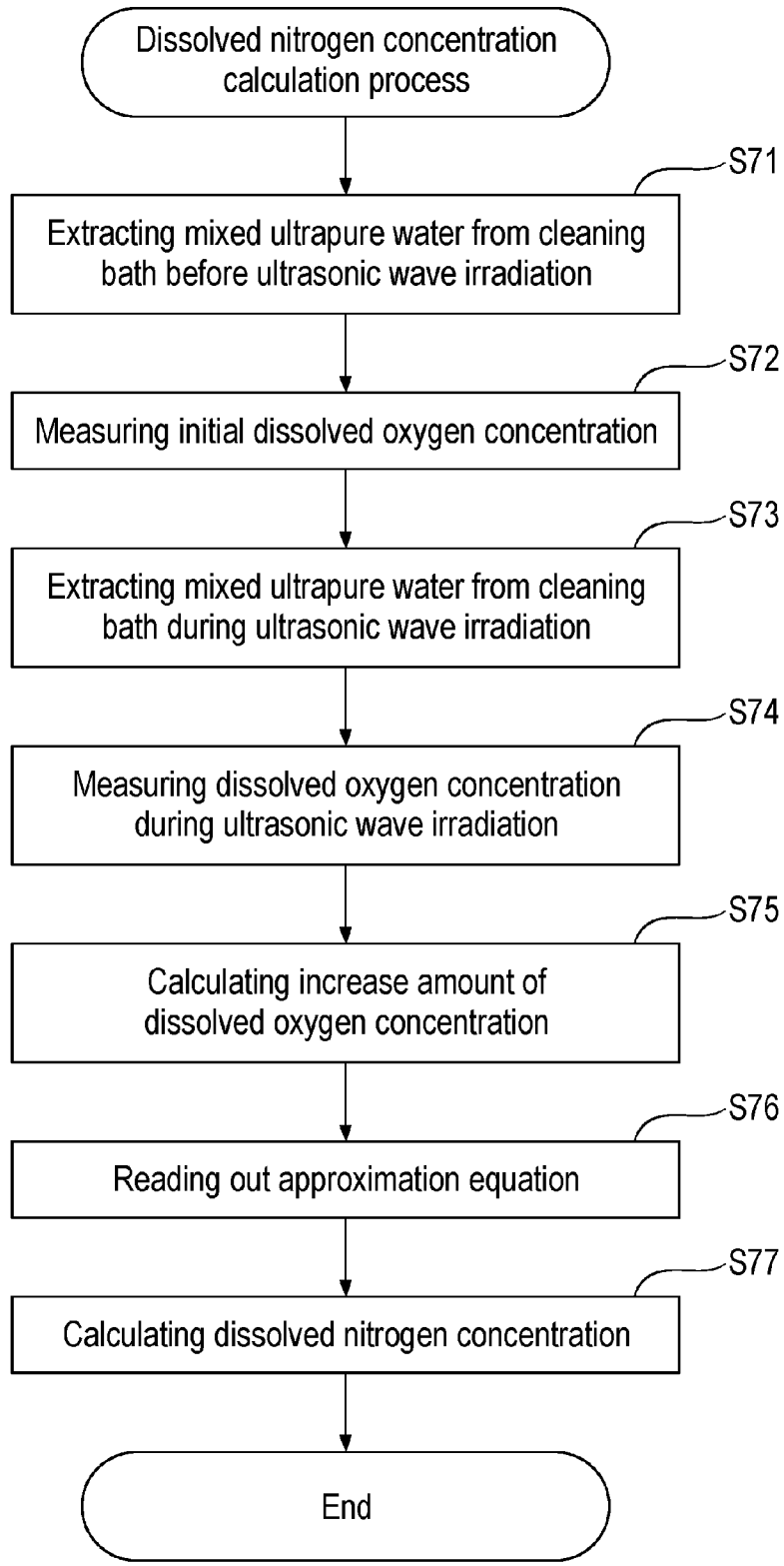
FIG. 7 is a flowchart showing a dissolved nitrogen concentration calculation process executed during performance of a monitoring method according an embodiment of the present invention.

The control section 47 performs overall control of each section of the monitoring unit 40 and reads out a program stored in the storage section 46 to execute the below-described dissolved nitrogen concentration calculating process (FIG. 7).

The particle removal efficiency of a cleaning method using ultrasonic waves is affected by the dissolved nitrogen concentration of ultrapure water. Specifically, it is known that the particle removal efficiency for a wafer increases when the dissolved nitrogen concentration of a cleaning liquid is in a specific range. In view of this theory, the present inventors focused on dissolved oxygen concentration, which can be effortlessly measured at low costs, and found out a method for monitoring the dissolved nitrogen concentration of a cleaning liquid. In this method, the dissolved nitrogen concentration is calculated based on the dissolved oxygen concentration during irradiation of ultrasonic waves. The specifics of this monitoring method are explained in the text to follow.

Figure 3:
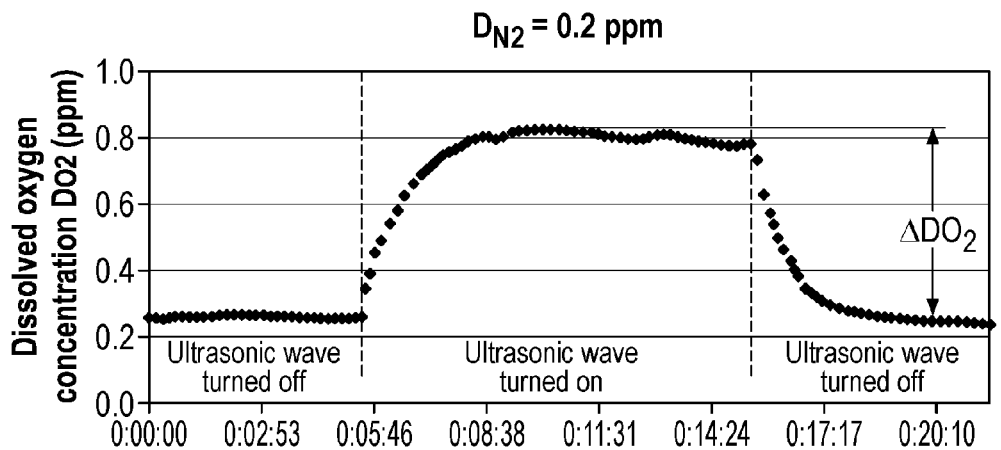
FIG. 3 is a diagram showing changes in the dissolved oxygen concentration of ultrapure water with a dissolved nitrogen concentration $D_{N2}$ of 0.2 ppm when ultrasonic waves are irradiated onto the ultrapure water.
Figure 4:
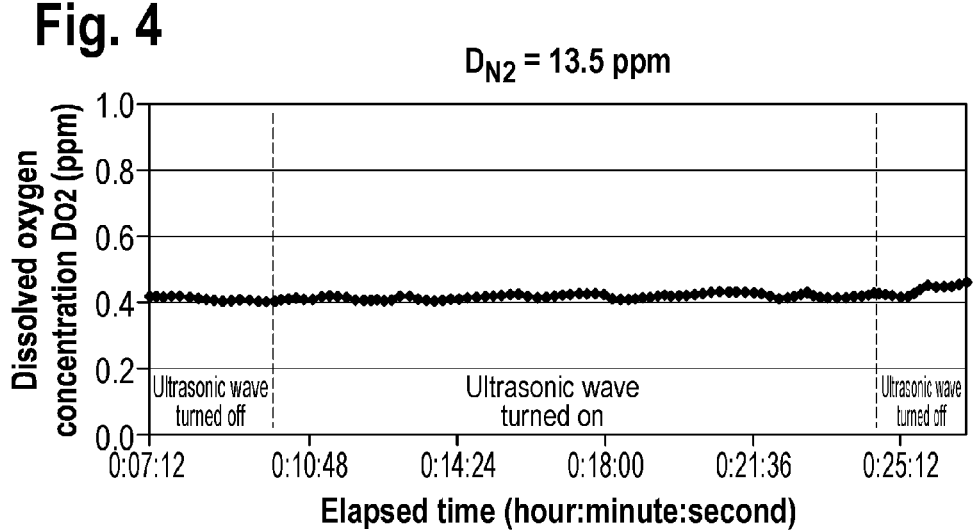
FIG. 4 is a diagram showing changes in the dissolved oxygen concentration of ultrapure water with a dissolved nitrogen concentration $D_{N2}$ of 13.5 ppm when ultrasonic waves are irradiated onto the ultrapure water.

First of all, the principle of this monitoring method is explained in reference to FIGS. 3 and 4. FIG. 3 is a diagram showing changes in the dissolved oxygen concentration of ultrapure water when ultrasonic waves are irradiated onto ultrapure water. In an example shown in FIG. 3, ultrapure water with a dissolved nitrogen concentration $D_{N2}$ of 0.2 ppm is used to explain changes in the dissolved oxygen concentration. The cleaning bath 20 in FIGS. 3 and 4 is a rectangular water bath made of 3.0 mm-thick plates of quartz glass. The internal dimensions of this bath were 270 mm wide×69 mm deep×270 mm high, and its capacity was 5 L. The volume of ultrapure water supplied to the cleaning bath 20 is 5 L/min. The frequency and output power level of the used ultrasonic waves were 950 kHz and 1200 W (watt density 5.6 W/cm2), respectively. The irradiated area of a vibration plate was 80 mm×270 mm, and ultrasonic waves were irradiated onto the whole bottom surface of the cleaning bath 20.

As shown in FIG. 3, irradiation of ultrasonic waves onto ultrapure water with an initial dissolved oxygen concentration $\Delta D_0$ of approximately 0.25 ppm causes the dissolved oxygen concentration to increase to approximately 0.8 ppm. In this case, the value of the dissolved oxygen concentration $D_{O2}$, which is measured by the monitoring unit 40, minus the initial dissolved oxygen concentration $D_0$ measured prior to ultrasonic wave irradiation—i.e., the increase amount of dissolved oxygen concentration $\Delta D_{O2}$ ($=D_{O2}-D_0$)—is 0.55 ppm. Subsequently, upon termination of ultrasonic wave irradiation, the dissolved oxygen concentration of the ultrapure water decreases to the level of the initial dissolved oxygen concentration. The above trends show that the dissolved oxygen concentration of ultrapure water is increased by ultrasonic wave irradiation.

FIG. 4 is a diagram showing changes in the dissolved oxygen concentration of ultrapure water when ultrasonic waves are irradiated onto ultrapure water. In this case, the dissolved nitrogen concentration $D_{N2}$ is 13.5 ppm.

As shown in FIG. 4, when the dissolved nitrogen concentration $D_{N2}$ of the ultrapure water is 13.5 ppm, irradiation of ultrasonic waves onto the ultrapure water does not cause the dissolved oxygen concentration to change since a reaction to produce oxygen molecules from water molecules is hindered by the presence of dissolved nitrogen. The dissolved oxygen concentration stays at the level of the initial dissolved oxygen concentration where ultrasonic waves are not irradiated. In this case, the increase amount of dissolved oxygen concentration $\Delta D_{O2}$ is 0 ppm.

It is possible to conclude from FIGS. 3 and 4 that during ultrasonic wave irradiation, as the dissolved nitrogen concentration of ultrapure water decreases, the amount of oxygen produced in the ultrapure water increases, and the dissolved oxygen concentration increases. When a radical reaction by the ultrasonic wave irradiation advances in the ultrapure water and water molecules are decomposed into hydrogen radicals and hydroxyl radicals, the hydroxyl radicals produce oxygen that is responsible for the aforementioned increases.

If an equation representing the relationship between the dissolved nitrogen concentration of ultrapure water and the increase amount of dissolved oxygen concentration thereof during ultrasonic wave irradiation is predetermined, this equation can be used to calculate the dissolved nitrogen concentration $D_{N2}$. The dissolved nitrogen concentration $D_{N2}$ corresponds to the increase amount of dissolved oxygen concentration $\Delta D_{O2}$ measured by the dissolved oxygen concentration meter 43. The dissolved nitrogen concentration of the ultrapure water can be monitored by performing the aforementioned calculation. For example, if changes in the increase amount of dissolved oxygen concentration $\Delta D_{O2}$ are monitored, the increase and decrease in the dissolved nitrogen concentration $D_{N2}$ can be monitored using the above equation. If the increase amount of dissolved oxygen concentration $\Delta D_{O2}$ corresponding to an arbitrary dissolved nitrogen concentration $D_{N2}$ is calculated and the increase amount of dissolved oxygen concentration of a cleaning liquid $\Delta D_{O2}$ is monitored, it is possible to determine whether the dissolved nitrogen concentration of the cleaning liquid is greater, smaller, or equal to the arbitrary dissolved nitrogen concentration $D_{N2}$.

The present inventors conducted a survey to identify factors influencing the relationship between the dissolved nitrogen concentration $D_{N2}$ of ultrapure water and the increase amount of dissolved oxygen concentration thereof $\Delta D_{O2}$. The survey identified that this relationship is influenced by the following factors: (1) the output power level of ultrasonic waves irradiated onto the ultrapure water; and (2) the overflow rate of ultrapure water supplied to the cleaning bath 20. The text to follow explains the relationship between $D_{N2}$ and $\Delta D_{O2}$ at different ultrasonic output power levels and at different overflow rates of ultrapure water.

FIGS. 5(*a*) and (*b*) are diagrams that indicate a relationship between the dissolved nitrogen concentration $D_{N2}$ of ultrapure water and the increase amount of dissolved oxygen concentration thereof $\Delta D_{O2}$ for each ultrasonic output power level. FIG. 5(*a*) is a diagram plotting measurements of the ultrasonic output power levels. FIG. 5(*b*) is a diagram depicting approximation equations for each ultrasonic output power levels.

Figure 5A:
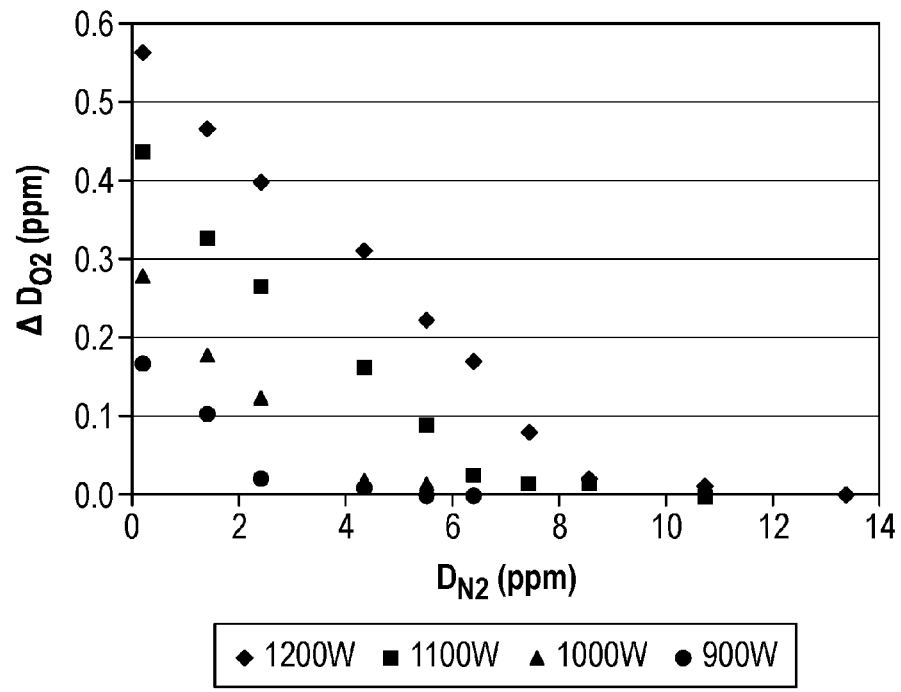
FIGS. 5(a) and (b) are diagrams that indicate a relationship between the dissolved nitrogen concentration $D_{N2}$ of ultrapure water and the increase amount of dissolved oxygen concentration thereof $\Delta D_{O2}$ for each ultrasonic output power level.
Figure 5B:
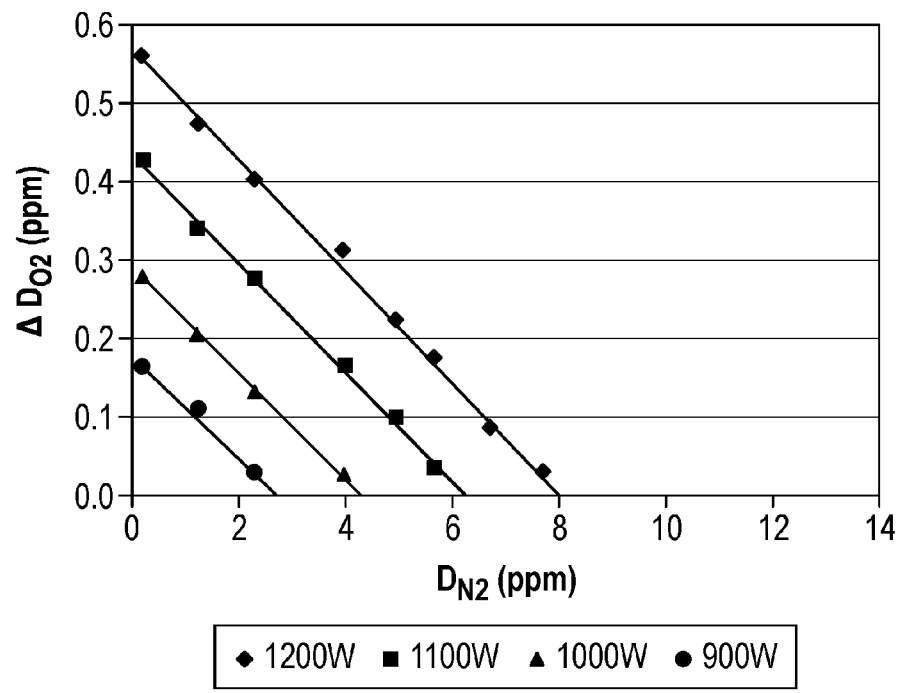
FIG. 5(b) is a diagram depicting approximation equations for each ultrasonic output power level.

FIG. 5(*a*) depicts the results of selecting 900 W (watt density: 4.2 W/cm2), 1000 W (watt density: 4.6 W/cm2), 1100 W (watt density: 5.1 W/cm2), and 1200 W (watt density: 5.6 W/cm2) as ultrasonic output power levels and plotting values indicating the relationship between $D_{N2}$ and $\Delta D_{O2}$ at the above output power levels. Approximation equations (calibration curves) determined from the plotted values have the slopes and y-intercepts presented in the drawing (FIG. 5(b)). The plotted values of FIG. 5(a) were obtained from measurement conducted using the cleaning bath 20, which is a rectangular water bath made of 3.0 mm-thick plates of quartz glass. The internal dimensions of this bath were 270 mm wide×69 mm deep×270 mm high, and its capacity is 5 L. The volume of ultrapure water supplied to the cleaning bath 20 was 5 L/min. The frequency of the used ultrasonic waves was 950 kHz. The irradiated area of a transducer was 80 mm×270 mm, and ultrasonic waves were irradiated onto the whole bottom surface of the cleaning bath 20.

When the output power level is 1200 W When the output power level is 1100 W

When the output power level is 1000 W $$y=-0.0639x+0.5667\ y=-0.0631x+0.4268$$

$$y=-0.0606x+0.2789$$

When the output power level is 900 W 000 y=−0.0607x+0.1763 (where y denotes the increase amount of dissolved oxygen concentration $\Delta D_{O2}$, and x denotes the dissolved nitrogen concentration $D_{N2}$)

The above results indicate a proportional relationship between the dissolved nitrogen concentration $D_{N2}$ and the increase amount of dissolved oxygen concentration $\Delta D_{O2}$. The slopes of the approximation equations are almost equal, and the y-intercept increases with an increase in the ultrasonic output power level. As the ultrasonic output power level increases, the increase amount of dissolved oxygen concentration corresponding to a specific dissolved nitrogen concentration increases. By increasing the ultrasonic output power level, the calculatable value of the dissolved nitrogen concentration increases, and the accuracy of measurement thereof increases.

Figure 6A:
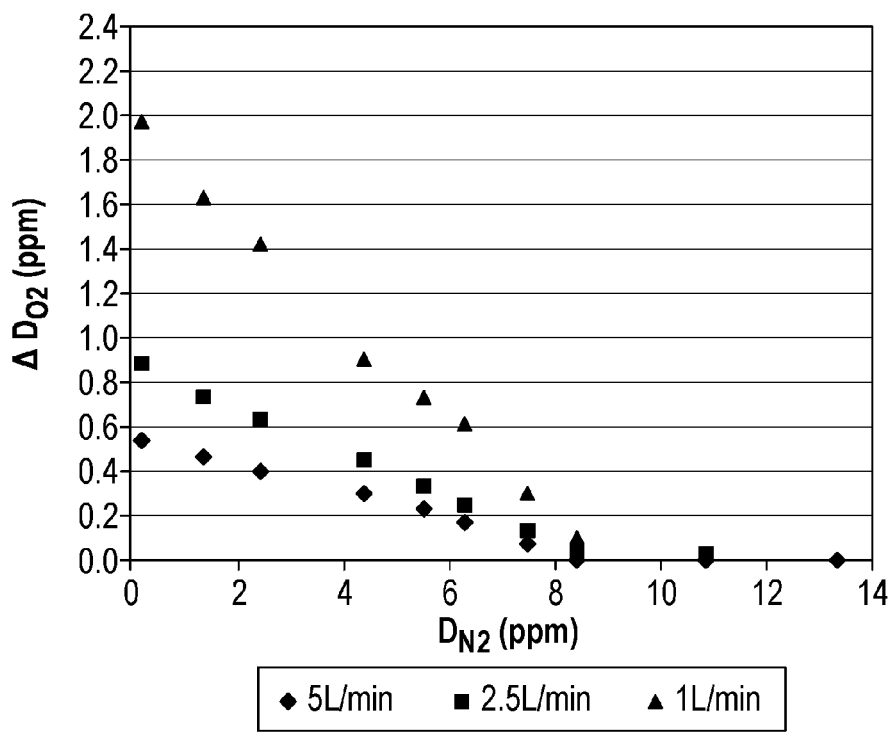
FIGS. 6(a) and (b) are diagrams that indicate a relationship between the dissolved nitrogen concentration $D_{N2}$ of ultrapure water and the increase amount of dissolved oxygen concentration thereof $\Delta D_{O2}$ for each overflow rate of ultrapure water.
Figure 6B:
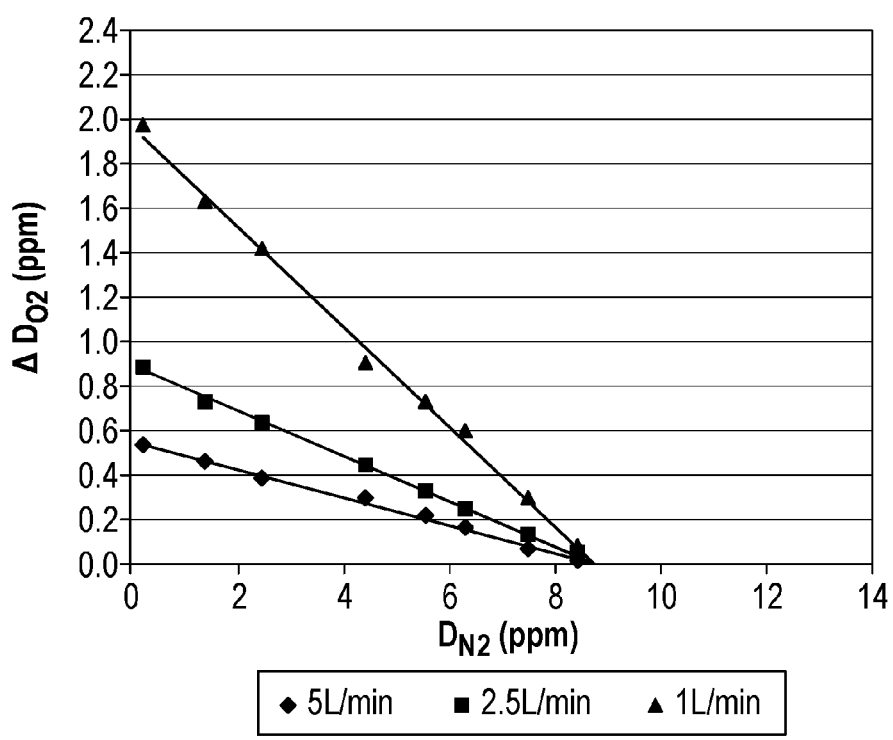
FIG. 6(b) is a diagram depicting approximation equations of overflow rates.

FIGS. 6(a) and (b) are diagrams that indicate the relationship between the dissolved nitrogen concentration $D_{N2}$ of ultrapure water and the increase amount of dissolved oxygen concentration thereof $\Delta D_{O2}$ for each overflow rate of ultrapure water. FIG. 6(a) is a diagram plotting each measurement of the overflow rates. FIG. 6(b) is a diagram depicting approximation equations of overflow rates.

FIG. 6(a) depicts the results of selecting 5 L/min, 2.5 L/min, and 1 L/min as overflow rates of ultrapure water and plotting values indicating the relationship between $D_{N2}$ and $\Delta D_{O2}$ at the above overflow rates. Approximation equations determined from the plotted values have the slopes and y—intercepts presented in the drawing (FIG. 6(b)). The plotted values of FIG. 6(a) were obtained from measurement conducted using the cleaning bath 20, which is a rectangular water bath made of 3.0 mm-thick plates of quartz glass. The internal dimensions of this bath were 270 mm wide×69 mm deep×270 mm high, and its capacity is 5 L. The frequency and output power level of the used ultrasonic waves were 950 kHz and 1200 W (watt density: 5.6 W/cm2), respectively. The irradiated area of a transducer was 80 mm×270 mm, and ultrasonic waves were irradiated onto the whole bottom surface of the cleaning bath 20.

When the overflow rate is 1 L/min 000 y=−0.2222x+1.956

When the overflow rate is 2.5 L/min 000 y=−0.0971x+0.868

When the overflow rate is 5 L/min 000 y=−0.069x+0.5667 (where y denotes the increase amount of dissolved oxygen concentration $\Delta D_{O2}$, and x denotes the dissolved nitrogen concentration $D_{N2}$)

The above approximation equations demonstrate that their slopes and y-intercepts increase with a decrease in the overflow rate of ultrapure water. As the overflow rate of the ultrapure water decreases, the rate of change in the increase amount of dissolved oxygen concentration increases with respect to the dissolved nitrogen concentration. By decreasing the overflow rate, the accuracy of measurement of the dissolved nitrogen concentration increases.

It is preferable to compile in advance dissolved gas information, as shown in FIGS. 3 and 4, on cleaning conditions, such as ultrasonic output power level and overflow rate, and to store the compiled information in the storage section 46. An approximation equation that corresponds to the ultrasonic output power level or overflow rate actually used in a wafer cleaning process can be selected from the dissolved gas information stored in the storage section 46. By substituting the measured increase amount of dissolved oxygen concentration $\Delta D_{O2}$ into the approximation equation, the dissolved nitrogen concentration $D_{N2}$ of ultrapure water can be accurately calculated.

FIG. 7 is a flowchart of a dissolved nitrogen concentration calculation process executed during performance of the monitoring method according to the embodiment of the present invention.

As shown in FIG. 7, before irradiating ultrasonic waves onto the cleaning bath 20, a predetermined amount of mixed ultrapure water is extracted from the cleaning bath 20 (step S71). Then the dissolved oxygen concentration meter 43 is used to measure the initial dissolved oxygen concentration $D_0$ prior to ultrasonic wave irradiation (step S72). Next, while ultrasonic waves at a predetermined output power level are irradiated onto the cleaning bath 20, a predetermined amount of mixed ultrapure water is extracted from the cleaning bath 20 (step S73), and the dissolved oxygen concentration $D_{O2}$ during ultrasonic wave irradiation is measured by the dissolved oxygen concentration meter 43 (step S74). In turn, the increase amount of dissolved oxygen concentration $\Delta D_{O2}$ is calculated by subtracting the initial dissolved oxygen concentration $D_0$ from the measured dissolved oxygen concentration $D_{O2}$ (step S75). Subsequently, an approximation equation corresponding to the predetermined overflow rate or ultrasonic output power level is read out from the storage section 46 (step S76), and the approximation equation read out from the storage section 46 is used to calculate the dissolved nitrogen concentration $D_{N2}$ of the mixed ultrapure water from the increase amount of dissolved oxygen concentration $\Delta D_{O2}$ measured in step S75 (step S77).

Upon completion thereof, the dissolved nitrogen concentration calculation process is terminated.

As described above, according to the embodiment of the present invention, the increase amount of dissolved oxygen concentration $\Delta D_{O2}$, which is due to a radical reaction in a cleaning liquid irradiated with ultrasonic waves, is measured. In turn, the dissolved nitrogen concentration $D_{N2}$ of the cleaning liquid is calculated from the measured increase amount of dissolved oxygen concentration $\Delta D_{O2}$ based on a predetermined relationship between the dissolved nitrogen concentration and the increase amount of dissolved oxygen concentration. Namely, as the dissolved nitrogen concentration $D_{N2}$ can be calculated by measuring the dissolved oxygen concentration $D_{O2}$ of the cleaning liquid, complicated operations are exempted. Also, since the relationship between the dissolved nitrogen concentration and the increase amount of dissolved oxygen concentration is predetermined, this relationship can be used to accurately calculate the dissolved nitrogen concentration $D_{N2}$. In addition, cost reduction is possible as an expensive dissolved nitrogen concentration meter does not need to be used. As well as cost reduction, accurate monitoring of the dissolved nitrogen concentration $D_{N2}$ of the cleaning liquid can be achieved without complicated operations.

In the above embodiment, the dissolved oxygen concentration meter 43 is of the polarography type. However, the type of dissolved oxygen concentration meter is not limited to the polarography type. It may be of the galvanic cell type.

Also, in the above embodiment, the cleaning liquid is ultrapure water, but the type of the cleaning liquid is not limited to ultrapure water. It may be generally used water. Any cleaning liquid whose dissolved oxygen can be accurately measured by a dissolved oxygen concentration meter of the polarography type or the like may be used. A mixed solution of hydrogen peroxide and ammonia (SC-1, APM) with a high ability to remove particles and organic contaminant may be used as well.

Furthermore, in the above embodiment, a wafer W is cleaned as the target substrate of the cleaning process, but it is not limited to the wafer W. Another substrate, such as a glass substrate for liquid crystal display or hard disk drives, may be cleaned as well.

Moreover, in the above embodiment, the mixture ratio of ultrapure water with dissolved nitrogen gas (the first supply valve 11) to degassed ultrapure water (the second supply valve 12) is adjusted to produce a cleaning liquid with dissolved nitrogen gas. However, the above embodiment is not limited thereto. The dissolved nitrogen concentration of ultrapure water may be directly adjusted by adjusting the pressure of nitrogen gas dissolved in the ultrapure water using a regulator (not shown) or the like.

For the above embodiment, focus was placed on an increase in the particle removal efficiency of a semiconductor wafer when the dissolved nitrogen concentration of ultrapure water is in a specific range. Accordingly, the dissolved nitrogen concentration was calculated from the increase amount of the dissolved nitrogen concentration $\Delta D_{O2}$ in the ultrapure water. In addition, to survey the relationship between the increase amount of the dissolved oxygen concentration $\Delta D_{O2}$ in ultrapure water and the particle removal efficiency of a semiconductor wafer, the present inventors conducted the following experiment:

(1) Production of Silicon Wafer Intentionally Contaminated for Particle Removal Efficiency Measurement A p-type silicon wafer with a diameter of 200 mm was dipped in hydrofluoric acid with a concentration of 0.5% for five minutes to remove a native oxide film from a surface thereof so that it is hydrophobic.

In a silicon nitride powder of Ube Industries, Ltd. (SN-E10, average particle diameter: 0.5 pm) was dispersed in 20 L of an aqueous hydrochloric acid solution (pH=2) at 50° C. so that the concentration is 0.05 ppm. Into the solution, the aforementioned silicon wafer was dipped for one minute.

Thereafter, rinsing was performed in ultrapure water for ten minutes, and drying was performed by a spin drier for two minutes.

(2) Measurement of Particle Removal Efficiency

Next, the number of particles adhered to a silicon wafer surface was measured using a particle counter (LS-6500 by Hitachi DECO). On the surface of the aforementioned silicon wafer intentionally contaminated for particle removal efficiency measurement produced in (1) above, approximately 8000 particles with a diameter of 0.1 pm or greater were adhered.

The number of particles was measured before and after the silicon wafer cleaning experiment described in (3) below. Based on the measurements before and after the experiment, particle removal efficiency was calculated using the following equation:

(Particle removal efficiency)={(Number of particles before cleaning)−(Number of particles after cleaning)}/(Number of particles before cleaning)×100 (%)

(3) Silicon Wafer Cleaning Experiment

The silicon wafer cleaning experiment was conducted using the ultrasonic cleaning apparatus shown in FIG. 1.

The cleaning bath 20 is a rectangular water bath made of 3.0 mm-thick plates of quartz glass. The internal dimensions of this bath are 270 mm wide×69 mm deep×270 mm high, and its capacity is 5 L. The supply flow rate of ultrapure water supplied to the cleaning bath 20 was 5 L/min. The frequency of the used ultrasonic waves was 950 kHz, and the output was 1200 W (watt density: 5.6 W/cm2). The irradiated area of a transducer was 80 mm×270 mm, and ultrasonic waves were irradiated onto the whole bottom surface of the cleaning bath 20.

The amount of the valve opening of the first supply valve 11 that supplies ultrapure water with dissolved nitrogen gas and that of the second supply valve 12 that supplies degassed ultrapure water were adjusted. The dissolved nitrogen concentration and flow rate of the ultrapure water to be supplied to inside the cleaning bath 20 were thereby controlled. The flow rate was controlled to be 5 L/min. Ultrasonic waves were irradiated onto the ultrapure water in the cleaning bath 20. The value of $\Delta D_{O2}$ was measured by the monitoring unit 40. A dissolved oxygen concentration meter of the polarography type was used as the dissolved oxygen concentration meter 43. The amount of the valve opening of the first supply valve 11 that supplies ultrapure water with dissolved nitrogen gas and that of the second supply valve 12 that supplies degassed ultrapure water were adjusted so that the $\Delta D_{O2}$ values are 0 ppm, 0.05 ppm, 0.1 ppm, 0.2 ppm, 0.3 ppm, 0.35 ppm, 0.4 ppm, and 0.5 ppm. The cleaning experiment was conducted at these eight $\Delta D_{O2}$ values.

After the $\Delta D_{O2}$ value is stabilized, the silicon wafer intentionally contaminated for particle removal efficiency measurement produced in (1) above was dipped for ten minutes and subsequently dried by a spin drier for two minutes.

(4) Results

Figure 8:
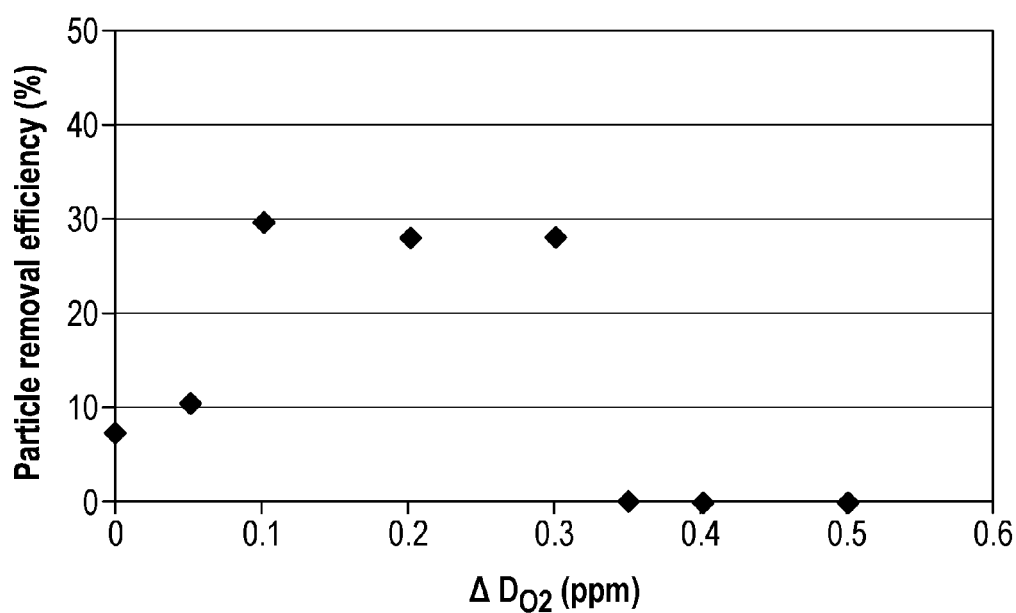
FIG. 8 is a diagram showing the relationship between the increase amount of the dissolved oxygen concentration $\Delta D_{O2}$ and the particle removal efficiency.

FIG. 8 shows the relationship between $\Delta D_{O2}$ and the particle removal efficiency obtained from the results of the cleaning experiment. The particle removal efficiency is found to be high in the $\Delta D_{O2}$ value range between 0.1 and 0.3 ppm.

When the ultrasonic cleaning apparatus of the present invention is used under the conditions of the cleaning experiment, the mixture ratio of ultrapure water with dissolved nitrogen gas (the first supply valve 11) to degassed ultrapure water (the second supply valve 12) was adjusted so that the $\Delta D_{O2}$ value ranges between 0.1 and 0.3 ppm. It is found that by making such an adjustment, cleaning with a high particle removal efficiency is possible without using a dissolved nitrogen concentration meter.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B." Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise.

EXPLANATION OF REFERENCE NUMERALS 1 ultrasonic cleaning apparatus
10 supply unit
20 cleaning bath
21 coupling bath
30 irradiation unit
40 monitoring unit
41 sampling pipe
42 pump
43 dissolved oxygen concentration meter
44 determination unit
45 receiving section
46 storage section
47 control section
48 display

The invention claimed is:

1. A dissolved nitrogen concentration monitoring method for monitoring a dissolved nitrogen concentration of a cleaning liquid when an ultrasonic wave is irradiated onto the cleaning liquid in which a substrate is dipped, the method comprising:
measuring an amount of increase of a dissolved oxygen concentration of the cleaning liquid resulting from an oxygen molecule generated from a water molecule as a result of a radical reaction caused by said irradiated ultrasonic wave; and
calculating a dissolved nitrogen concentration of the cleaning liquid from the measured amount of increase of dissolved oxygen concentration based on a predetermined relationship between the dissolved nitrogen concentration and the amount of increase of dissolved oxygen concentration.

2. The dissolved nitrogen concentration monitoring method according to claim 1, wherein:
the amount of increase of dissolved oxygen concentration is measured by a dissolved oxygen concentration meter.

3. The dissolved nitrogen concentration monitoring method according to claim 1, wherein:
dissolved gas information indicating the relationship between the dissolved nitrogen concentration and the amount of increase of dissolved oxygen concentration is compiled in advance for each of a plurality of cleaning conditions of the substrate.

4. The dissolved nitrogen concentration monitoring method according to claim 1, wherein:
the cleaning liquid is water.

5. The dissolved nitrogen concentration monitoring method according to claim 3, wherein:
the plurality of cleaning conditions of the substrate includes an ultrasonic output power level.

6. The dissolved nitrogen concentration monitoring method according to claim 3, wherein:
the cleaning conditions of the substrate includes an overflow rate of the cleaning liquid.

7. The dissolved nitrogen concentration monitoring method according to claim 5, wherein:
dissolved gas information indicating the relationship between the dissolved nitrogen concentration and the amount of increase of dissolved oxygen concentration indicates that as the ultrasonic output power level increases, the amount of increase of dissolved oxygen concentration corresponding to a specific dissolved nitrogen concentration increases.

8. The dissolved nitrogen concentration monitoring method according to claim 6, wherein:
dissolved gas information indicating the relationship between the dissolved nitrogen concentration and the amount of increase of dissolved oxygen concentration indicates that as the overflow rate decreases, a rate of change in the amount of increase of dissolved oxygen concentration increases with respect to the dissolved nitrogen concentration.

9. A method for cleaning a substrate by irradiating an ultrasonic wave onto a cleaning liquid disposed in a cleaning bath in which the substrate is dipped, the method comprising:
introducing a cleaning liquid into the cleaning bath, the cleaning liquid including a mixture ratio of a first liquid and a second liquid, the first liquid comprising dissolved nitrogen gas;
determining a measured amount of an increase of a dissolved oxygen concentration of the cleaning liquid resulting from an oxygen molecule generated from a water molecule as a result of a radical reaction caused by said irradiated ultrasonic wave; and
adjusting the mixture ratio of the cleaning liquid with the dissolved nitrogen gas being introduced into the cleaning bath so as to achieve a target amount of increase of the dissolved oxygen concentration in a specific range.

* * * * *